United States Patent
Cox et al.

(10) Patent No.: US 11,278,512 B2
(45) Date of Patent: Mar. 22, 2022

(54) COMPOSITIONS COMPRISING A METAL AND L-SERINE, AND USES THEREOF

(71) Applicant: Brain Chemistry Labs, Jackson, WY (US)

(72) Inventors: Paul Alan Cox, Jackson, WY (US); Sandra Anne Banack, Jackson, WY (US); James S. Metcalf, Jackson, WY (US); Rachael Dunlop, Jackson, WY (US)

(73) Assignee: BRAIN CHEMISTRY LABS, Jackson, WY (US)

( * ) Notice: Subject to any disclaimer, the term of this patent is extended or adjusted under 35 U.S.C. 154(b) by 0 days.

(21) Appl. No.: 16/999,305

(22) Filed: Aug. 21, 2020

(65) Prior Publication Data

US 2021/0052533 A1   Feb. 25, 2021

Related U.S. Application Data

(60) Provisional application No. 62/890,000, filed on Aug. 21, 2019.

(51) Int. Cl.
*A61K 31/198* (2006.01)
*A61P 25/28* (2006.01)
*A61K 33/30* (2006.01)
*A61K 33/242* (2019.01)

(52) U.S. Cl.
CPC .......... *A61K 31/198* (2013.01); *A61K 33/242* (2019.01); *A61K 33/30* (2013.01); *A61P 25/28* (2018.01)

(58) Field of Classification Search
CPC .... A61K 31/198; A61K 33/242; A61K 33/30; A61P 25/28
See application file for complete search history.

(56) References Cited

U.S. PATENT DOCUMENTS

| | | |
|---|---|---|
| 6,337,094 B1 | 1/2002 | Guardiola et al. |
| 2003/0096414 A1 | 5/2003 | Ciccarone et al. |
| 2005/0287204 A1 | 12/2005 | Hageman et al. |
| 2007/0258892 A1 | 11/2007 | Tallberg |
| 2013/0156846 A1* | 6/2013 | Rodgers ................. A61P 25/20 424/450 |
| 2017/0304195 A1* | 10/2017 | Foger ................... A61K 38/095 |

FOREIGN PATENT DOCUMENTS

WO   WO-2011022350 A1 *   2/2011   ............. A61K 33/30
WO   WO-2017068548 A1 *   4/2017   ........... A23K 20/147

OTHER PUBLICATIONS

Patent Cooperation Treaty, International Search Report issued in PCT/US2020/047219, dated Nov. 19, 2020, pp. 1-3.
Ramani et al., "Amino acid-mediated synthesis of zinc oxide nanostructures andevaluation of their facet-dependent antimicrobial activity", Colloids and Surfaces B: Biointerfaces, 2014, pp. 233-239, vol. 117.
Van Der Helm et al., "The Crystal Structure of Bis(L-serinato)zinc", Acta Cryst, 1970, pp. 1172-1178, B26.

\* cited by examiner

*Primary Examiner* — Robert A Wax
*Assistant Examiner* — Olga V. Tcherkasskaya
(74) *Attorney, Agent, or Firm* — Pillsbury Winthrop Shaw Pittman LLP

(57) ABSTRACT

Presented herein are compositions comprising L-serine, or a precursor, derivative or conjugate thereof, and a non-toxic metal, such as zinc. Compositions disclosed herein can be used for the prevention and treatment of neurodegenerative diseases, or related symptoms thereof.

13 Claims, 1 Drawing Sheet

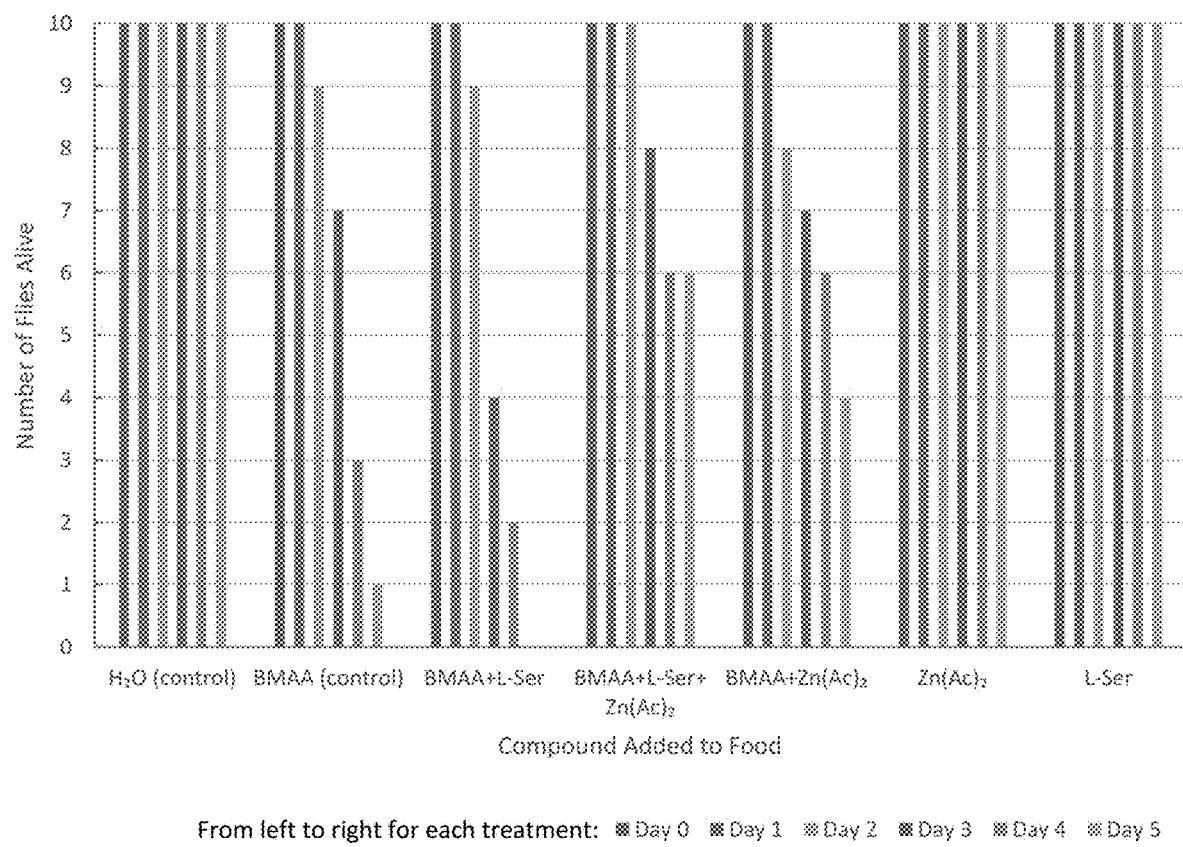

COMPOSITIONS COMPRISING A METAL AND L-SERINE, AND USES THEREOF

RELATED PATENT APPLICATIONS

This patent application claims the benefit of U.S. Provisional Patent Application No. 62/890,000 filed on Aug. 21, 2019, entitled COMPOSITIONS COMPRISING A METAL AND L-SERINE, AND USES THEREOF. The entire content of the foregoing application is incorporated herein by reference, including all text, tables and drawings.

BACKGROUND

Neurodegeneration is the progressive loss of structure or function of neurons. Many neurodegenerative diseases such as amyotrophic lateral sclerosis, Parkinson's disease, Alzheimer's disease, Lewy Body disease, Progressive Supranuclear Palsy, and Huntington's disease occur as a result of neurodegenerative processes. Presented herein are compositions and methods for the prevention and/or treatment of neurodegenerative disease.

SUMMARY

Provided herein, in some aspects, is a composition comprising a non-toxic metal, such as zinc, and L-serine, or a precursor, derivative or conjugate thereof, for use in preventing or treating a neurodegenerative disease. In some aspects, provided herein, is a method of preventing or treating a neurodegenerative disease in a subject comprising administering to the subject a therapeutically effective amount of a composition comprising zinc and L-serine, or a precursor, derivative or conjugate thereof. In some embodiments, a neurodegenerative disease is selected from Alzheimer's disease (AD), Dementia, Frontotemporal Dementia (FTD), Chronic Traumatic Encephalopathy (CTE), Pick's Disease, Parkinson's disease (PD) and PD-related disorders, Prion disease, amyotrophic lateral sclerosis (ALS), Huntington's disease (HD), Spinocerebellar ataxia (SCA), Spinal muscular atrophy (SMA), ALS-PDC (amyotrophic lateral sclerosis-Parkinsonism dementia complex), Lewy Body disease, Progressive Supranuclear Palsy (PSP), Mild Cognitive Impairment (MCI), Age-Associated Memory Impairment (AAMI), Age Related Cognitive Decline (ARCD), chemotherapy-induced cognitive dysfunction, amnestic MCI (aMCI) and Friedreich's ataxia. In some embodiments, the method comprises ameliorating, suppressing, inhibiting or reducing one or more symptoms of the neurodegenerative disease selected from cognitive deficiency; cognitive decline, fatigue; passivity; lethargy; inertia; tremors; ataxia; speaking difficulty; muscle cramps, twitching, atrophy or weakness; shortness of breath; breathing difficulty; short term memory loss; long term memory loss; difficulty concentrating; difficulty completing familiar or routine tasks; space and time confusion; vision, color or sign recognition loss; depth perception loss, writing difficulty; loss of reading comprehension; loss of judgment; vocabulary loss; moodiness; unusual or frequent irritability; unusual or frequent aggression; paranoia; delusions; withdrawal from social engagement; unusual or frequent stiffness or rigidity; loss of fine or gross motor control; slowing of movement; impaired balance; body instability; posture or gait abnormality; reduced coordination; motor dysfunction; jerky or involuntary body movement; slowed saccadic eye movement; seizures; difficulty chewing, eating, or swallowing; deterioration in cognition/mental capabilities; dementia; irregular sleep, insomnia, sleep disruption; diagnosed behavioral or psychiatric abnormalities; impaired regulation of social conduct; social withdrawal; over-activity; pacing; wandering; loss of balance; lunging forward when mobilizing; fast walking; imbalance; falls; changes in personality; loss of inhibition or ability to organize information; opthalmoparesis or impaired eye movement; impaired eyelid function; involuntary facial muscle contracture; neck dystonia or backward tilt of the head with stiffening of neck muscles; urinary/bowel incontinence; and parkinsonism.

In some aspects provided herein is also a method for altering the up or down regulation of biomarkers associated with neurodegenerative diseases, including microRNA fingerprints with unequivocal signatures of neurodegeneration including those derived from neurally-enriched exosome extraction such as miR-146a-5p, miR-4454, miR-199a, miR199a-3p, miR-10b-5p, miR-29, miR-151a-3p, miR-151a-5p, and miR-199a-5p; and changes in amino acid ratios from blood serum or other unique metabolites which appear as biomarkers for progressive neurodegenerative illness.

BRIEF DESCRIPTION OF THE DRAWINGS

FIG. 1 shows the graphical experimental results of treatment of fruit flies with L-serine and zinc. The y-axis shows the number of flies that were alive at the end of the experiment as indicated by the colored bars. The x-axis indicates the treatment groups, from left to right (i.e., Group 0 control (H2O (Control)), Group 1 control (BMAA (control)), Group 2 (BMAA+L-ser), Group 3 (BMAA+L-ser+Zn(Ac)2), Group 4 (BMAA+Zn(Ac)2), Group 5 Zn(Ac)2), and Group 6 (L-ser).

DETAILED DESCRIPTION

Cyanobacteria produce β-methylamino-L-alanine (BMAA), which can be incorporated into mammalian proteins. The incorporation of BMAA into certain proteins of the brain and/or central nervous system can lead to undesirable protein misfolding, protein aggregation and consequent neuronal disorders and neurodegenerative diseases characterized by protein aggregation, tangles and/or plaques. L-serine blocks misincorporation of BMAA into human neuroproteins, reduces protein misfolding, protein aggregation and subsequent apoptosis induced by BMAA. In non-human primates, L-serine decreases the density of neurofibrillary tangles (NFTs) and β-amyloid plaques in the brain. L-serine also blocks BMAA-induced microglial activation and proteinopathies along the spine, including deposition of TDP-43 and FUS, which in humans is indicative of the earliest stages of ALS. Therefore, L-serine can be used to prevent, and/or treat neuro-dysfunction, neurodegeneration, certain neurodegenerative diseases and symptoms thereof. Without being limited to theory, we propose that misincorporation of BMAA into proteins may be inhibited by the presence of L-serine during translation, thereby inhibiting or slowing the onset or progression of neurodegeneration.

It has been demonstrated that BMAA binds exceptionally strongly to transition metal ions such as zinc, copper, and iron. If BMAA is capable of crossing over the blood brain barrier (BBB), such that it can enter a compartment where glutamate/zinc complexes are present, then it is possible that a glutamate/zinc complex might dissociate in favor of zinc having a stronger affinity to BMAA. This could lead to higher levels of unbound glutamate (free glutamate) which is believed to be highly neurotoxic in ALS patients. Without being limited to theory, we hypothesize that exposing patients to high levels of zinc would allow both BMAA and glutamate to form complexes with zinc, thereby reducing levels of free glutamate.

Zinc has been approved by the FDA for chelation therapy for patients with Wilson's disease. Zinc was also shown to be safe when administered to ALS patients at up to 90 mg/day (Clinical Trials.gov identifier: NCT01259050) and has been shown to have an approximate 30% reduction in ALSFRS (Amyotrophic Lateral Sclerosis Functional Rating Scale) after daily dosing with 90 mg/ml zinc for three months, which approximates the reduction achieved by Riluzole.

As disclosed herein, in some embodiments, administering a combination of L-serine and zinc to a subject having a neurodegenerative disorder can provide for an enhanced, synergistic therapeutic effect.

Embodiments disclosed herein generally related to compositions comprising L-serine, or a salt, a precursor, derivative or conjugate thereof, and zinc, and uses thereof for the prevention and treatment of neurodegenerative disease. In certain embodiments, the compositions disclosed herein comprise formulations and nanoparticles comprising L-serine and zinc. In some embodiments, a method is disclosed that comprises administering L-serine, or a salt, a precursor, derivative or conjugate thereof, and zinc to a subject for the prevention and/or treatment of neurodegenerative diseases and/or for reducing one or more symptoms of said diseases.

Neurodegenerative Diseases

In certain aspects, provided herein are methods of preventing or treating a neurogenerative disease. Non-limiting examples of a neurogenerative disease that can be prevented or treated by a method disclosed herein include Alzheimer's disease (AD), Dementia, Frontotemporal Dementia (FTD), Chronic Traumatic Encephalopathy (CTE), Pick's Disease, Parkinson's disease (PD) and PD-related disorders, Prion disease, amyotrophic lateral sclerosis (ALS), Huntington's disease (HD), Spinocerebellar ataxia (SCA), Spinal muscular atrophy (SMA), ALS-PDC (amyotrophic lateral sclerosis-Parkinsonism dementia complex), Lewy Body disease, Progress Supranuclear Palsy (PSP), Mild Cognitive Impairment (MCI), Age-Associated Memory Impairment (AAMI), Age Related Cognitive Decline (ARCD), chemotherapy-induced cognitive dysfunction, amnestic MCI (aMCI) and Friedreich's ataxia. In some embodiments, a method of preventing or treating a neurodegenerative disease includes preventing, treating, ameliorating, delaying the onset of, suppressing, inhibiting and/or reducing one or more symptoms of a neurodegenerative disease, non-limiting examples of which symptoms include a motor or cognitive deficiency; cognitive decline, fatigue (e.g., excessive fatigue); passivity; lethargy; inertia; tremors; ataxia; speaking difficulty (e.g., slurred, thick or irregular speech); muscle cramps (e.g., excessive muscle cramping, not necessarily induced by excessive use or excessive exercise), twitching, atrophy or weakness; shortness of breath; breathing difficulty; short term memory loss; long term memory loss; difficulty concentrating; difficulty completing familiar or routine tasks; space and time confusion; vision, color or sign recognition loss; depth perception loss, writing difficulty; loss of reading comprehension; loss of judgment; vocabulary loss; moodiness; unusual or frequent irritability; unusual or frequent aggression; paranoia; delusions; withdrawal from social engagement; unusual or frequent stiffness or rigidity; loss of fine or gross motor control; slowing of movement; impaired balance; body instability; posture or gait abnormality (e.g., shuffling walk, unsteady or irregular gait); reduced coordination; motor dysfunction; jerky or involuntary body movement; slowed saccadic eye movement; seizures; difficulty chewing, eating, or swallowing; deterioration in cognition/mental capabilities; dementia; irregular sleep, insomnia, sleep disruption; diagnosed behavioral or psychiatric abnormalities; impaired regulation of social conduct; social withdrawal; over-activity; pacing; wandering; loss of balance; lunging forward when mobilizing; fast walking; imbalance; falls; changes in personality; loss of inhibition or ability to organize information; opthalmoparesis or impaired eye movement; impaired eyelid function; involuntary facial muscle contracture; neck dystonia or backward tilt of the head with stiffening of neck muscles; urinary/bowel incontinence; parkinsonism; the like and combinations thereof. Accordingly, in certain embodiments, provided herein is a method of treating, preventing, ameliorating, delaying the onset of, suppressing, inhibiting and/or reducing one or more symptoms of a neurodegenerative disease by administering to a subject a composition disclosed herein. In certain embodiments, a method comprises reducing the severity of and/or reducing the frequency of one or more symptoms of a neurodegenerative disease. In certain embodiments, a method comprises preventing exacerbation of, and/or worsening of one or more symptoms of a neurodegenerative disease.

In some embodiments, a method herein inhibits, reduces, and/or suppresses the severity or frequency of one or more symptoms of neurodegeneration, including but limited to cognitive decline, cognitive dysfunction, and/or loss of memory in a subject. In some embodiments, a method herein inhibits, reduces, and/or suppresses the severity or frequency of one or more symptoms of neurodegeneration by an amount of at least 5%, 10%, 15%, 20%, 25%, 35%, 40%, 45%, 50%, such as from about 1%) to 100%, from 2% to 100%, from 5% to 100%, from 10% to 100%, from 20% to 100%, from 30% to 100%, or from about 40% to 100% compared to a measure of severity or frequency of one or more symptoms prior to conducting a method disclosed herein. In some embodiments, a method herein delays the onset of neurodegeneration, or delays the onset of one or more symptoms of neurodegeneration. In some embodiments, an inhibition of cognitive decline or loss of memory is an improvement in cognitive ability and/or an increase in memory, for example as compared to a measure of cognitive ability or memory determined prior to conducting a method disclosed herein. In some embodiments, an inhibition of cognitive decline is an absence of further cognitive decline, or in some embodiments, no change in cognitive decline. In some embodiments, an inhibition of loss of memory is an absence of further loss of memory, or in some embodiments, no change in memory.

In some embodiments, changes in the onset, severity or frequency of a symptom of neurodegeneration is determined by a suitable subjective or objective assessment of a subject's cognitive function. In some embodiments, cognitive function (e.g., including memory and learning) and/or changes in cognitive function (e.g., cognitive decline, cognitive impairment, loss of memory, and/or learning ability) is determined by, or assessed by a subject's performance in one or more suitable cognitive tests, non-limiting examples of which include measures of attention, processing speed, executive function, social interaction, fine motor skills, speech, physical ability to move, memory, psychometric tests, neurological tests, problem solving tests, counting tests, language tests, global ability, combinations thereof, and the like. Additional non-limiting examples of cognitive tests that can be used to assess cognitive function include the Mini-Mental State Examination (MMSE) (e.g., see Saczynski et al., (2012) N. Engl. J. Med. 367:30-39); the Reliable Change Index (e.g., see Lewis et al., (2006) Acta Anaesthesiol Scand. 50:50-57; and Berger et al., (2015) Anesthesiol Clin. 33(3):517-50); the Rey Auditory Verbal Learning Tests; Trail Making Tests, Parts A & B; the Grooved Peg Board Test; the Digit Span Tests; the Stroop Tests, the Four-Field Tests, Erzigkeit's Short Cognitive Performance Test; and a patient's self-assessment. In certain embodiments, cognitive function, or changes thereof, is measured by comparing the results of a suitable medical evaluation or cognitive test conducted before and/or after administering a composition disclosed herein. Additional non-limiting examples of medical evaluations of neurodegeneration, symptoms thereof, and/or cognitive decline include brain computed tomography (CT), magnetic resonance imaging (MRI) scans, single photon emission computed tomography (SPECT), FDG-PET scans, and the like. In some embodiments, cognitive decline is self-reported by a subject (e.g., complains of memory loss), or is determined through observation of a subject's behavior by another.

In certain aspects, provided herein are methods of enhancing cognitive function (e.g., an increase in cognitive function; cognitive enhancement) in a subject, the method comprising administering to the subject a composition disclosed herein. Non-limiting examples of enhancing cognitive function include an increase in memory and\or an increase in learning. In some embodiments, an enhancement of cognitive function is demonstrative by an increase in the level of at least one aspect of cognitive function over a baseline level prior to conducting a method described herein. In some embodiments, cognitive enhancement is achieved in a subject when the subject shows improvement in one or more tests of cognitive function after completion of a method disclosed herein. For example, in some embodiments, cognitive enhancement is achieved in a subject when a subject's memory or learning ability is enhanced compared to an amount of memory or learning ability prior to administration of a composition described herein. In some embodiments, cognitive enhancement is assessed by comparison to a placebo treatment.

In some embodiments, a method described herein enhances cognitive function in healthy subjects (e.g., a subject not diagnosed with a neurodegenerative disease or cognitive dysfunction) by administering a composition disclosed herein.

Compositions

In some embodiments, provided herein are compositions comprising two active pharmaceutical ingredients, one of which is a non-toxic metal and the other is L-serine or a salt, a precursor, derivative or conjugate thereof. Non-limiting examples of a non-toxic metal include iron, calcium, copper, zinc, gold, magnesium, selenium and salts thereof. In some embodiments, a composition comprises or consists essentially of zinc, or salt thereof, and L-serine or a salt, a precursor, derivative or conjugate thereof, and uses thereof. In some embodiments, a composition consisting essentially of zinc and L-serine, free L-serine, or a salt, a precursor, derivative or conjugate thereof, is a composition that comprises zinc and L-serine, free L-serine, or a salt, a precursor, a derivative or a conjugate thereof as the only two active ingredients (e.g., active pharmaceutical ingredients (APIs)) in the composition. Accordingly, a composition consisting essentially of zinc and L-serine, free L-serine, or a salt, a precursor, a derivative or a conjugate thereof may include various pharmaceutical excipients, additives, carriers and/or diluents. In some embodiments, a composition consisting essentially of zinc and L-serine, free L-serine, or a salt, a precursor, a derivative or a conjugate thereof excludes proteins or protein fractions comprising less than 100%, 99%, 98%, less than 95%, less than 90%, less than 80%, less than 70%, less than 60%, or less than 50% L-serine (wt/wt). In some embodiments, a composition consisting essentially of zinc and L-serine, free L-serine, or a salt, a precursor, a derivative or a conjugate thereof excludes proteins or protein fractions comprising greater than 5%, greater than 10%, greater than 20%, greater than 30%, greater than 40%, greater than 50% or greater than 60% protein (wt/wt). In some embodiments, a composition consisting essentially of zinc and L-serine comprises free L-serine, or a polymer of L-serine having an amino acid content of L-serine of at least 100%, 99%, 98%, 95%, 90%, 85% or at least 80%. In some embodiments, a composition consisting essentially of zinc and L-serine excludes creatine, creatine pyruvate, guanidino-acetic acid (GA), glycocyamine, N-amidinoglycine, and salts or esters thereof. In some embodiments, a composition consisting essentially of zinc and L-serine is a composition comprising free L-serine at a purity of at least 85%, at least 90%, at least 95%, at least 98%, at least 99% or 100%. In certain embodiments, a composition consisting essentially of L-serine, free L-serine, or a salt, a precursor, derivative or conjugate of L-serine, is a composition that also comprises zinc.

In some embodiments, a composition comprises free-L-serine. Free L-serine refers to L-serine in the form of a single amino acid monomer, or a salt thereof. In some embodiments, a composition comprises free L-serine at a purity of at least 85%, at least 90%, at least 95%, at least 98%, at least 99% or 100%. In certain embodiments, free L-serine is not covalently bonded to any other amino acid.

In some embodiments, a composition may exclude other active ingredients. In some embodiments, a composition may exclude proteins containing L-serine. In some embodiments, a composition may exclude proteins having a molecular weight greater than 10 kDa, greater than 20 kDa, greater than 30 kDa or greater than 50 kDa. In some embodiments, a composition may exclude proteins containing less than 99%, 98%, 95%, 92%, 90%, 80%, 70%, 60%, or less than 50% L-serine. In some embodiments, a composition may exclude creatine, or any energy metabolism precursor of creatine, such as guanidino-acetic acid (GA), equivalents thereof, and mixtures thereof.

In certain embodiments, a composition comprises L-serine, non-limiting examples of which include free L-serine, and polymers or polypeptides comprising at least a 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% L-serine by weight or amino acid content. In some embodiments, a polymer of L-serine or a polypeptide comprising L-serine includes between 2 and 50000, between 2 and 500, between 2 and 100, between 2 and 50, between 2 and 20, between 2 and 15, between 2 and 10, between 2 and 9, between 2 and 8, between 2 and 7, between 2 and 6, between 2 and 5, or between 2 and 4 L-serine amino acids linked by covalent bonds. In certain embodiments, a composition comprises L-serine, non-limiting examples of which include a polymer or polypeptide comprising from 20% to 100%, from 30% to 100%, from 35% to 100%, from 40% to 100%, from 45% to 100%, from 50% to 100%, from 55% to 100%, from 60% to 100%, from 65% to 100%, from 70% to 100%, from 75% to 100%, from 80% to 100%, from 85% to 100%, from 90% to 100%, from 95% to 100%, from 96% to 100%, from 97% to 100%, from 98% to 100%, or from 99% to 100% content of L-serine (wt/wt) or amino acid content (i.e., L-serine monomers/total amino acid monomers).

In some embodiments, a composition comprises a suitable derivative of L-serine. In certain embodiments, a composition comprises a salt of L-serine, non-limiting examples of which include a sodium salt, potassium salt, calcium salt, magnesium salt, zinc salt, ammonium salt; inorganic salts such as, hydrogen chloride, sodium chloride, potassium chloride, calcium chloride, sodium phosphate, potassium phosphate, and sodium hydrogen carbonate; organic salts such as, sodium citrate, citrate, acetate, and the like. In certain embodiments, a composition comprises L-serine as an alkylated L-serine, such as L-serine with an alkyl group, or e.g., an alkyl comprising 1-20 carbon atoms. In certain embodiments, a derivative of L-serine includes an L-serine ester, an L-serine di-ester, a phosphate ester of L-serine, or a sulfate or sultanate ester of L-serine. Non-limiting examples of a conjugate of L-serine includes a pegylated L-serine (e.g., an L-serine comprising one or more polyethylene glycol (PEG) moieties), and a lipidated L-serine. Non-limiting example of a precursor of L-serine include L-phosphoserine.

In certain embodiments, a composition comprises a precursor of L-serine, non-limiting examples of which include a pro-form of L-serine that is broken down into L-serine monomers by the digestive system of a subject. In some embodiments, L-serine or a conjugate thereof consists of a slow-release version. In some embodiments a derivative of L-serine is conjugated to a different molecule forming a prodrug from which L-serine is released after crossing the blood/brain barrier.

Amino acids can be present in D or L stereoisometric forms (enantiomers). In some embodiments, a composition consisting essentially of L-serine may comprise some amount of D-serine. For example, a composition of the present disclosure may include a small amount of D-serine, for example, less than 30%, less than 25%, less than 20%, less than 15%, less than 10%, less than 9%, less than 8%, less than 7%, less than 6%, less than 5%, less than 4%, less than 3%, less than 2%, less than 1%, less than 0.9%, less than 0.8%, less than 0.7%, less than 0.6%, less than 0.5%, less than 0.4%, less than 0.3%, less than 0.2%, or less than 0.1% D-serine by weight (e.g., wt/wt) or amino acid content (e.g., L-serine/total amino acid content). For example, a composition may include from 0.001% to 30%, from 0.005% to 30%, from 0.1% to 30%, from 1% to 30%, from 2% to 30%, from 3% to 30%, from 4% to 30%, from 5% to 30%, from 6% to 30%, from 7% to 30%, from 8% to 30%, from 9% to 30%, from 10% to 30%, from 0.001% to 20%, from 0.005% to 0%, from 0.1% to 20%, from 1% to 20%, from 2% to 20%, from 3% to 20%, from 4% to 20%, from 5% to 20%, from 6% to 20%, from 7% to 20%, from 8% to 20%, from 9% to 20%, or from 10% to 20% D-serine. In some embodiments, a composition comprising or consisting essentially of L-serine, does not comprise a substantial amount of D-serine. In some embodiments, a composition comprising or consisting essentially of L-serine, does not contain D-serine.

In some embodiments, a composition comprises a non-toxic metal selected from iron, calcium, copper, zinc, gold, magnesium, selenium and salts thereof. In some embodiments, a composition comprises a non-toxic metal such as zinc. In some embodiments, a composition comprises zinc and L-serine, or a salt, a precursor, derivative or conjugate thereof. In some embodiments, a composition comprises zinc and free L-serine. In some embodiments, a composition comprises zinc and consists essentially of L-serine, or a salt, a precursor, derivative or conjugate thereof.

In some embodiments, a composition disclosed herein does not include a substantial amount of cadmium. In some embodiments, a composition or formulation disclosed herein contains less than 10%, less than 5%, less than 2%, less than 1%, less than 0.5%, less than 0.25%, less than 0.1%, less than 0.01% or less than 0.001% cadmium per weight. In certain embodiments, a composition or formulation disclosed herein comprises less than 100 micrograms, less than 50 micrograms, less than 10 micrograms, less than 2 micrograms, less than 1 microgram, or less than 0.1 micrograms of cadmium, for example per dose (e.g., single dose, daily dose, or weekly dose) and/or formulation (e.g., per capsule, per tablet).

A composition disclosed herein may comprise a non-toxic metal, such as zinc, in any suitable form (e.g., a form suitable for administration to a subject), non-limiting examples of which include a pharmaceutically acceptable salt thereof selected from one or more of the following counterions: chloride, sulfate, oxide, carbonate, citrate, acetate, lactate, glutamate, gluconate, picolinate, aspartate, benzoate, bromide, camsylate, edetate, glycolate, malate, maleate, lactobionate, nitrate, oleate, octanoate, pamoate, phosphate, polygalacturonate, propionate, salicylate, stearate, succinate, tartrate, teoclate, tosylate, the like, and combinations thereof. In some embodiments, a composition comprises a suitable form or salt of zinc (e.g., zinc chloride, zinc sulfate, zinc citrate, zinc acetate, zinc lactate, zinc glutamate, zinc gluconate, and zinc picolinate), and a conjugate of zinc. In some embodiments, a composition comprises a non-toxic metal as a metal complex (e.g., a metal salt complex, a metal oxide complex, metal amino acid complex). In some embodiments, a composition comprises zinc as a zinc complex (e.g., a zinc oxide complex, zinc amino acid complex). In some embodiments, a composition comprises a nanoparticle comprising a non-toxic metal, such as zinc. In some embodiments, a composition comprises a nanoparticle comprising a non-toxic metal (e.g., zinc) and L-serine. In some embodiments, a metal/L-serine nanoparticle (e.g., a zinc/L-serine nanoparticle) is generated using a variation of the method of Wangoo et al., (2008) *J. of Colloid and Interface Science* 323(2), p. 247-254, which is incorporated herein by reference. For example, in certain embodiments, zinc (e.g., $Zn^{+2}$) is combined with L-serine to form a zinc/L-serine nanoparticle seed which can be capped at a desired size to permit optimum bioavailability with a resultant decrease in dose necessary to achieve neuroprotection.

Subjects

The term "subject" refers to a mammalian animal. Any suitable mammal can be treated by a method described herein. Non-limiting examples of mammals include humans, non-human primates (e.g., apes, gibbons, chimpanzees, orangutans, monkeys, macaques, vervets, marmosets, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. A mammal can be any age or at any stage of development (e.g., an adult, teen, child, or infant). A mammal can be male or female. In some embodiments, a subject is a pregnant female. In some embodiments, a subject is not a pregnant female. In certain embodiments, a subject is a human in the age range of 1 year to 55 years, 1 year to 50 years, 1 year to 45 years, 1 year to 40 years, 1 year to 21 years. In certain embodiments, a subject is a human over the age of 50. In certain embodiments, a subject is a man over the age of 50. In certain embodiments, a subject is a woman over the age of 50. In certain embodiments, a subject is a post-menopausal woman. In certain embodiments, a subject is a human in need of a composition or method disclosed herein. In certain embodiments, a subject is a human having, or suspected of having, a neurodegenerative disease, or a human experiencing one or more symptoms of a neurodegenerative disease.

In certain embodiments, a composition disclosed herein is administered to a subject that does not have a disease or disorder selected from diabetes (e.g., Type I or Type II diabetes), insulin resistance, epilepsy, neuropathy, nerve damage, chronic pain, chronic fatigue syndrome, macular degeneration, night blindness, HIV/AIDS, hyperbilirubinemia, anorexia nervosa, obsessive compulsive disorder, dry mouth, attention deficit hyperactivity disorder (ADHD), hypogeusia, hepatic encephalopathy, alcohol-related liver disease, Crohn's disease, colitis (e.g., ulcerative colitis), inflammatory bowel disease (IBD), canker sores, stomach ulcer, bed sores, leg ulcers, encephalopathy, enlarged prostate, erectile dysfunction, depression, osteoporosis, arthritis (e.g., rheumatoid arthritis), muscle cramps (e.g., muscle cramps caused by a liver disease), thalassemia, Down syndrome, Hansen's disease, cystic fibrosis, cancer, anemia, chronic obstructive pulmonary disease, burns, leprosy, leishmania, warts, herpes, bad breath, a parasitic infection, an amino acid deficiency, an inability to make L-serine, and a zinc deficiency. In certain embodiments, a subject does not have a disorder selected from ALS, AD, ALS\PDC, dementia, PD, HD, PSP and Lewy body dementia (LBD). In certain embodiments, a subject does not have Alzheimer's disease (AD). In certain embodiments, a subject does not have a disease or disorder associated with a glucose deficiency (e.g., a deficiency of glucose in the central nervous system). In certain embodiments, a subject does not have a disease or disorder associated with decreased function or levels of a glucose transporter (e.g., GLUT1 and/or GLUT3 levels).

Dose and Therapeutically Effective Amount

Methods and uses of the present disclosure include administering a therapeutically effective amount of a composition disclosed herein to a subject. In some embodiments, a composition comprises a therapeutically effective amount of zinc and a therapeutically effective amount of L-serine, or a conjugate, salt, derivative or precursor thereof. In certain embodiments, a therapeutically effective amount is an amount that, upon administration to a subject, is intended to achieve a therapeutic effect. In some embodiments, a therapeutically effective amount of a compound or composition for use in a method described herein is an amount needed to obtain an effective therapeutic outcome. In certain embodiments, a therapeutically effective amount is an amount sufficient to prevent or treat a neurodegenerative disease. In certain embodiments, a therapeutically effective amount is an amount sufficient to ameliorate, suppress, reduce or inhibit one or more symptoms of a neurodegenerative disease. In certain embodiments, a therapeutically effective amount is an amount sufficient to inhibit or delay cognitive decline in a subject, enhance cognitive function in a subject, or enhance memory or learning ability in a subject.

In certain embodiments, a therapeutically effective amount is an amount high enough to provide an effective therapeutic effect (e.g., a beneficial therapeutic effect) and an amount low enough to minimize unwanted adverse reactions. Accordingly, in certain embodiments, a therapeutically effective amount of a composition for use in a method described herein may vary from subject to subject, often depending on age, weight, and/or a general health condition of a subject. Thus, in some embodiments, a therapeutically effective amount is determined empirically. Accordingly, a therapeutically effective amount of a composition for use in a method described herein that is administered to a subject can be determined by one of ordinary skill in the art based on amounts found effective in animal or clinical studies, a physician's experience, and suggested dose ranges or dosing guidelines, for example, as disclosed herein.

In certain embodiments, a therapeutically effective amount is an amount of a composition disclosed herein, administered at dosages and/or for periods of time necessary to achieve a desired and/or beneficial consequence of a method disclosed herein. In certain embodiments, a therapeutically effective amount of a composition disclosed herein is administered at a suitable dose (e.g., at a suitable volume, frequency and/or concentration, which often depends on a subject's weight, age and/or condition) intended to obtain an acceptable therapeutic outcome. In certain embodiments, a therapeutically effective amount of a composition disclosed herein comprises one or more doses (administered to a subject) of a composition comprising at least 0.1 mg/kg, at least 5 mg/kg, at least 10 mg/kg, at least 15 mg/kg, at least 20 mg/kg, at least 25 mg/kg, at least 50 mg/kg, at least 100 mg/kg, at least 250 mg/kg, at least 500 mg/kg, at least 1000 mg/kg, at least 5000 mg/kg, or at least 7500 mg/kg of L-serine, or a salt, a precursor, derivative or conjugate thereof, per kg body weight of a subject. In certain embodiments, a therapeutically effective amount of a composition disclosed herein comprises one or more doses (administered to a subject) of a composition comprising at least 0.0001 µg/kg, at least 0.001 µg/kg, at least 0.01 µg/kg, at least 0.1 µg/kg, at least 1 µg/kg, at least 5 µg/kg, at least 10 µg/kg, at least 15 µg/kg, at least 20 µg/kg, at least 25 µg/kg, at least 50 µg/kg, at least 100 µg/kg, or at least 250 µg/kg of zinc per kg body weight of a subject.

In certain embodiments, a composition, dose or formulation disclosed herein comprises at least 100 mg, at least 500 mg, at least 1 g, at least 5 g, at least 10 g, at least 20 g, at least 30 g, at least 40 g, at least 50 g, at least 60 g, at least 70 g, or at least 80 g of L-serine, or a salt, a precursor, derivative or conjugate thereof, and at least 0.01 mg, 0.1 mg, 1 mg, 2 mg, 4 mg, 5 mg, 8 mg, or 10 mg of zinc. In certain embodiments, a composition, dose or formulation disclosed herein comprises L-serine, or a salt, a precursor, derivative or conjugate thereof in an amount in a range of about 0.5-200 g, 10-100 g, 20-100 g, 71-200 g, 1-100 g, 1-90 g, 1-80 g, 1-70 g, 1-60 g, 1-30 g, or 1-25 g, and zinc in an amount in a range of about 0.01 mg-50 mg, 0.01 mg-25 mg, 0.1 mg-25 mg or 1 mg-25 mg.

In some embodiments administering a therapeutically effective amount of a composition disclosed herein comprises administering a suitable composition hourly, every two hours, every 4 hours, every 6 hours, every 8 hours, or every 12 hours. In certain embodiments, a composition disclosed herein can be administered at least one, at least two, at least three, at least four, at least five, or at least six times per day, e.g., 1 to 12 times per day, 1 to 8 times per day, or 1 to 4 times per day per day. In certain embodiments, a composition disclosed herein can be administered once, twice, 3 times, 4 times, 5 times, 6 times, 7 times, 8 times, 9 times, 10 times, 11 times, or 12 times per day. A composition may be administered in a single dosage form or one or more dosage forms. A daily dose can be achieved in the form of a single dose or in the form of a plurality of partial doses.

A composition disclosed herein can be administered on a daily basis or on a schedule containing days where dosing does not take place. For example, dosing may take place every other day, or dosing may take place for 2, 3, 4, or 5 consecutive days of a week, then be followed by from 1 to 5 non-dosing days.

A composition herein can be administered for at least a day, at least two days, at least three days, at least four days, at least five days, at least a week, at least two weeks, at least three weeks, at least a month, at least two months, at least three months, at least six months, at least a year, at least two years, or more, or for any extended duration to further improve, maintain, or retain therapeutic efficacy. In certain embodiments, a composition is administered for a duration of 1 week to 10 years or more.

Route of Administration

Any suitable method of administering a composition for use in a method described herein to a subject can be used. Any suitable formulation and/or route of administration can be used for administration of a composition or pharmaceutical composition for use in a method described herein (e.g., see Fingl et al. 1975, in "The Pharmacological Basis of Therapeutics", which is incorporated herein by reference in its entirety). A suitable formulation and/or route of administration can be chosen by a medical professional (e.g., a physician) in view of, for example, a subject's risk, age, and/or condition. Non-limiting examples of routes of administration include topical or local (e.g., transdermally or cutaneously, (e.g., on the skin or epidermis), in or on the eye, intranasally, transmucosally, in the ear, inside the ear (e.g., behind the ear drum)), enteral (e.g., delivered through the gastrointestinal tract, e.g., orally (e.g., as a tablet, capsule, granule, liquid, emulsification, lozenge, or combination thereof), sublingual, by gastric feeding tube, rectally, and the like), by parenteral administration (e.g., parenterally, e.g., intravenously, intra-arterially, intramuscularly, intraperitoneally, intradermally, subcutaneously, intracavity, intracranial, intra-articular, into a joint space, intracardiac (into the heart), intracavernous injection, intralesional (into a skin lesion), intraosseous infusion (into the bone marrow), intrathecal (into the spinal canal), intrauterine, intravaginal, intravesical infusion, intravitreal), the like or combinations thereof. In some embodiments, a composition disclosed herein is administered orally.

Formulations

Compositions disclosed herein can be administered in various forms or formulations. For example, where the compositions are to be administered orally, they may be formulated as powders, chewable dosage forms, beverage formulations, tablets, capsules, soft gels, gel caps, or liquids; or for parenteral administration, they may be formulated as injections (intravenous, intramuscular, or subcutaneous). In some embodiments, a composition disclosed herein is formulated as a powder or granules suitable for dissolving in an aqueous, ingestible solvent (e.g., water, coffee, juice, wine, beer, a sports drink, an energy drink, a nutrient drink, and the like).

Compositions suitable for oral administration may be presented as discrete units such as capsules, cachets, or tablets, soft gels, gel caps, chewable dosage units (e.g., chewable tablets, quick chew, gummy, jelly beans, lozenges, health bars, foods, cereal coatings, food supplements, nutritional supplements), each containing a therapeutically effective amount of the composition, as a powder or granules, or as a solution or a suspension in an aqueous liquid, as nanoparticles in either powdered or liquid suspended forms or in a non-aqueous liquid, an oil-in-water emulsion, or a water-in-oil liquid emulsion. In general, the compositions are prepared by homogenously admixing the active ingredients with liquid carriers or finely divided solid carriers or both, and then, if necessary, shaping the product into the desired presentation. In some embodiments a composition suitable for oral administration comprises a slow-release formulation.

A composition disclosed herein can additionally include one or more pharmaceutically acceptable excipients, diluents and other inactive ingredients such as binding agents (such as pregelatinized maize starch, polyvinylpyrrolidone or hydroxypropyl methylcellulose); binders or fillers (such as lactose, pentosan, microcrystalline cellulose or calcium hydrogen phosphate); lubricants (such as magnesium stearate, talc or silica); disintegrants (such as potato starch or sodium starch glycolate); or wetting agents (such as sodium lauryl sulphate).

In certain embodiments, a composition may be formulated as a beverage that, in some embodiments, is provided in a suitable container (e.g., a can, bottle or carton) and/or in a concentrated or ready-to-think formulation suitable for human consumption. In some embodiments, a beverage is prepared by mixing a composition disclosed herein in power form with a beverage, such as water, milk, any flavored beverages, or soda, for example, to provide a beverage formulation in which the composition (in powder form) is dispensed. In one embodiment, a beverage is prepared by mixing a composition disclosed herein in liquid form with a beverage to provide a beverage formulation in which the composition (in liquid form) is dispensed.

A unit dose form may be individually wrapped, packaged as multiple units, or in bottles, or vials of any size, without limitation.

In some embodiments, a composition or a pharmaceutical composition disclosed herein is provided to a subject. For example, a composition that is provided to a subject is sometimes provided to a subject for self-administration or for administration to a subject by another (e.g., a non-medical professional). As another example, a composition can be provided as an instruction written by a medical practitioner that authorizes a patient to be provided a composition or treatment described herein (e.g., a prescription). In yet another example, a composition can be provided to a subject where the subject self-administers a composition orally, or intravenously, for example.

Pharmaceutical compositions comprising, or consisting essentially of, zinc and L-serine, or a precursor, derivative or conjugate thereof, as described herein can be formulated in any suitable manner using one or more pharmaceutically acceptable carriers, non-limiting examples of which include carriers, solvents, salts, excipients, additives, preservatives, and/or auxiliaries. Proper formulation can depend upon the route of administration chosen. In particular, a pharmaceutical compositions can comprise any suitable carrier, formulation, or ingredient, the like or combinations thereof as listed in "Remington: The Science And Practice Of Pharmacy" Mack Publishing Co., Easton, Pa., 19$^{th}$ Edition, (1995), or "Remington: The Science And Practice Of Pharmacy", Pharmaceutical Press, Easton, Pa., 22$^{nd}$ Edition, (2013). The various materials listed herein, alone or in combination, can be incorporated into or used with the materials described in Remington's. Any suitable techniques, carriers, and excipients can be used, including those understood in the art; e.g., in Remington's Pharmaceutical Sciences, above.

In some embodiments, a composition comprising zinc and comprising or consisting essentially of, L-serine, or a precursor, derivative or conjugate thereof, as described herein, is formulated for oral administration as a slow release, or sustained release preparation. In some embodiments, a composition comprising zinc and comprising, or consisting essentially of, L-serine, or a precursor, derivative or conjugate thereof, as described herein, is a slow release or sustained release composition. Any suitable method of preparing a slow release or sustained release composition can be used. In some embodiments, a sustained release formulation comprises a gelling agent; at least one inert pharmaceutical diluent selected from the group consisting of monosaccharides, disaccharides, polyhydric alcohols, and mixtures thereof; and a pharmaceutically acceptable cationic cross-linking agent capable of crosslinking with the gelling agent.

EXAMPLES

A number of embodiments of the disclosure have been described. Nevertheless, one skilled in the art, without departing from the spirit and scope of the disclosure, can make various changes and modifications of the disclosure to adapt it to various usages and conditions. Accordingly, the following examples are intended to illustrate, but not limit, the scope of the disclosure claimed in any way. The following Examples serve as an illustration of embodiments disclosed herein. Amounts of L-serine expressed in the examples herein refer to amounts of the free form of L-serine, unless indicated otherwise.

Example I—Combining L-Serine and Zinc Acetate Results in Increased Reduction of Neurodegeneration Fruit flies were administered BMAA to induce neurodegeneration and were treated with nothing, L-serine, zinc acetate or a combination of L-serine and zinc acetate as shown in the study groups below. The experimental agents (i.e., BMAA, L-serine, and zinc) were administered by incorporation of the indicated amounts in the food:
  Group 0 (Control)—Administered water.
  Group 1 (Control)—Administered 25 mM BMAA.
  Group 2 (Treatment #1)—Administered 25 mM BMAA and 20 mM L-serine.
  Group 3 (Treatment #2)—Administered 25 mM BMAA, 20 mM L-serine and 5 mM zinc acetate.
  Group 4 (Treatment #3)—Administered 25 mM BMAA and 5 mM zinc acetate.
  Group 5 (Treatment #4)—Administered 5 mM zinc acetate.
  Group 6 (Treatment #5)—Administered 20 mM L-serine.
  The results show that a combination of L-serine with zinc acetate increases survival of fruit flies dosed with 25 mM BMAA (FIG. 1).

The entirety of each patent, patent application, publication or any other reference or document cited herein hereby is incorporated by reference. In case of conflict, the specification, including definitions, will control.

Citation of any patent, patent application, publication or any other document is not an admission that any of the foregoing is pertinent prior art, nor does it constitute any admission as to the contents or date of these publications or documents.

Unless otherwise defined, all technical and scientific terms used herein have the same meaning as commonly understood by one of ordinary skill in the art.

All of the features disclosed herein may be combined in any combination. Each feature disclosed in the specification may be replaced by an alternative feature serving a same, equivalent, or similar purpose. Thus, unless expressly stated otherwise, disclosed features (e.g., antibodies) are an example of a genus of equivalent or similar features.

As used herein, all numerical values or numerical ranges include integers within such ranges and fractions of the values or the integers within ranges unless the context clearly indicates otherwise. Further, when a listing of values is described herein (e.g., about 50%, 60%, 70%, 80%, 85% or 86%) the listing includes all intermediate and fractional values thereof (e.g., 54%, 85.4%). Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-50, 50-100, 100-1,000, 1,000-3,000, 2,000-4,000, etc.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

Some embodiments of the technology described herein suitably can be practiced in the absence of an element not specifically disclosed herein. Accordingly, in some embodiments the term "comprising" or "comprises" can be replaced with "consisting essentially of" or "consisting of" or grammatical variations thereof. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. The term, "substantially" as used herein, refers to a value modifier meaning "at least 95%", "at least 96%", "at least 97%", "at least 98%", or "at least 99%" and may include 100%. For example, a composition that is substantially free of X, may include less than 5%, less than 4%, less than 3%, less than 2%, or less than 1% of X, and/or X may be absent or undetectable in the composition.

The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

What is claimed is:

1. A therapeutic composition for oral administration to a subject having a neurodegenerative disease, the composition comprising:
   (i) zinc or gold in an amount of about 0.1 mg to 25 mg; and
   (ii) L-serine, or a polymer of L-serine, in an amount of at least 10 g.

2. The composition of claim 1, wherein the composition comprises L-serine having a purity of at least 95 wt. %.

3. The composition of claim 1, wherein the composition consists essentially of zinc and L-serine.

4. The composition of claim 1, where the zinc comprises zinc chloride or zinc acetate.

5. The composition of claim 1, where the zinc is in the form of a nanoparticle, wherein the nanoparticle is optionally formulated as a powder or suspended in a liquid or colloidal formulation.

6. The composition of claim 1, wherein the composition comprises about 1 mg to 25 mg of zinc and at least 20 g of L-serine.

7. The composition of claim 1, wherein the composition does not contain an energy metabolism precursor.

8. A method of treating neurodegeneration, or a neurodegenerative disease in a subject comprising administering to the subject a therapeutically effective amount of the composition of claim 1.

9. The method of claim 8, wherein the subject is a human.

10. The method of claim 8, wherein the composition comprises about 1 mg to 25 mg of zinc and at least 20 g of L-serine.

11. The method of claim 8, wherein the composition is administered to the subject orally in a dosage form selected from the group consisting of a chewable dosage form, a beverage formulation, a tablet, a capsule, a soft gel, a gel cap, a liquid and a colloidal suspension.

12. The method of claim 8, wherein the neurodegenerative disease is selected from the group consisting of Alzheimer's disease, dementia, frontotemporal dementia, Pick's disease, Parkinson's disease and Parkinson's disease related disorders, prion disease, amyotrophic lateral sclerosis, Huntington's disease, spinocerebellar ataxia, spinal muscular atrophy, amyotrophic lateral sclerosis-Parkinsonian dementia complex, Lewy Body disease, progressive supranuclear palsy, chronic traumatic encephalopathy, Glut1 deficiency syndrome, mild cognitive impairment, age-associated memory impairment, age related cognitive decline, chemotherapy induced cognitive dysfunction, amnestic mild cognitive impairment, and Friedreich's ataxia.

13. The method of claim 8, wherein the treating comprises ameliorating, suppressing, inhibiting or reducing one or more symptoms of the neurodegenerative disease selected from the group consisting of cognitive deficiency; cognitive decline, fatigue; passivity; lethargy; inertia; tremors; ataxia; speaking difficulty; muscle cramps, twitching, atrophy or weakness; shortness of breath; breathing difficulty; short term memory loss; long term memory loss; difficulty concentrating; difficulty completing familiar or routine tasks; space and time confusion; vision, color or sign recognition loss; depth perception loss, writing difficulty; loss of reading comprehension; loss of judgment; vocabulary loss; moodiness; unusual or frequent irritability; unusual or frequent aggression; paranoia; delusions; withdrawal from social engagement; unusual or frequent stiffness or rigidity; loss of fine or gross motor control; slowing of movement; impaired balance; body instability; posture or gait abnormality; reduced coordination; motor dysfunction; jerky or involuntary body movement; slowed saccadic eye movement; seizures; difficulty chewing, eating, or swallowing; deterioration in cognition/mental capabilities; dementia; irregular sleep, insomnia, sleep disruption; diagnosed behavioral or psychiatric abnormalities; impaired regulation of social conduct; social withdrawal; over-activity; pacing; wandering; loss of balance; lunging forward when mobilizing; fast walking; imbalance; falls; changes in personality; loss of inhibition or ability to organize information; opthalmoparesis or impaired eye movement; impaired eyelid function; involuntary facial muscle contracture; neck dystonia or backward tilt of the head with stiffening of neck muscles; urinary/bowel incontinence; and parkinsonism.

\* \* \* \* \*